(12) United States Patent
Dario et al.

(10) Patent No.: US 7,695,468 B2
(45) Date of Patent: Apr. 13, 2010

(54) ENDOSCOPIC SURGERY DEVICE

(75) Inventors: Paolo Dario, Leghorn (IT); Andrea Pietrabissa, Pisa (IT); Bernardo Magnani, Leghorn (IT); Cesare Stefanini, Cascina (IT)

(73) Assignee: Microtech S.R.L., Pisa (IT)

( * ) Notice: Subject to any disclaimer, the term of this patent is extended or adjusted under 35 U.S.C. 154(b) by 0 days.

(21) Appl. No.: 10/581,660

(22) PCT Filed: Nov. 23, 2004

(86) PCT No.: PCT/IT2004/000643

§ 371 (c)(1),
(2), (4) Date: Jun. 3, 2006

(87) PCT Pub. No.: WO2005/053589

PCT Pub. Date: Jun. 16, 2005

(65) Prior Publication Data

US 2007/0118074 A1     May 24, 2007

(30) Foreign Application Priority Data

Mar. 12, 2003   (IT) .................. FI2003A0310

(51) Int. Cl.
*A61F 13/20* (2006.01)
(52) U.S. Cl. ......................................... 606/11
(58) Field of Classification Search ........... 604/11–16, 604/104, 358, 362, 572; 606/213; 600/431, 600/572, 573
See application file for complete search history.

(56) References Cited

U.S. PATENT DOCUMENTS

| 3,698,393 A | 10/1972 | Stone ..................... 128/296 |
| 5,074,840 A | 12/1991 | Yoon ....................... 604/15 |
| 5,203,767 A | 4/1993 | Cloyd ....................... 604/11 |
| 5,310,407 A | 5/1994 | Casale ....................... 604/51 |
| 5,447,499 A | 9/1995 | Allaire et al. ................ 602/42 |
| 6,191,341 B1 | 2/2001 | Shippert ..................... 504/383 |
| 6,673,080 B2 * | 1/2004 | Reynolds et al. ............ 606/127 |
| 2003/0073969 A1 | 4/2003 | Klainer .................. 604/385.01 |

\* cited by examiner

*Primary Examiner*—Anhtuan T Nguyen
*Assistant Examiner*—Jennifer L Hornberger
(74) *Attorney, Agent, or Firm*—Pollack, P.C.

(57) ABSTRACT

An endoscopic surgery device for the insertion and recovery of a haemostatic plug at the surgical site. The device comprises a tubular body suitable for slidingly housing the plug, and a plunger slidingly engageable within the tubular body so as to push the plug outside the body, and to position it at the surgical site. The plug is connected to a locator that is radio-opaque, has a suitable color, and has a specific weight that allows it to float relative to the internal organs, blood or other fluids present at the surgical site. A loop is provided at a distal end of the plunger and at a proximal end of the plunger, a first handle is provided for actuating the plunger so as to grip the ball and recover the plug after use by retracting the plunger inside the tubular body.

9 Claims, 2 Drawing Sheets

ENDOSCOPIC SURGERY DEVICE

FIELD OF THE INVENTION

The present invention relates generally to medical instruments and, more particularly, to devices for use in endoscopic surgery and the like.

BACKGROUND OF THE INVENTION

Endoscopic surgery, i.e., minimally invasive access to a cavity of a patient's body, such as the abdominal cavity, is typically performed through the use of miniaturized optical and surgical instruments. In the case of laparoscopic surgery, which concerns the peritoneal cavity, the cavity is essentially virtual from the surgeon's perspective and cannot be explored by optical instruments. To provide the cavity with more substance or space, its walls are raised by insufflation of gas, generally $CO_2$, to form a gas chamber, known as a pneumoperitoneum. Access to the pneumoperitoneal chamber is accomplished using trocars or small incisions that are fit with a valve, so that communication between the interior and exterior of the abdomen occurs without significant variation in actual pressure of the gas. Surgical instruments may then be inserted through the trocars with optics connected externally to a television camera and, in turn, to a monitor, thereby forming a take and image transmission system.

Even if the pressure exerted on the patient's organs by the pneumoperitoneum causes spontaneous haemostasis of countless capillaries as may have been lesioned in forming the pneumoperitoneum, it is considered necessary that perfect haemostasis be achieved throughout. Otherwise, visibility inside the cavity may be so reduced as to make it impossible, or at least inadvisable, to continue laparoscopic surgery without risk to the patient's safety. Normally, during laparoscopic procedures, outflowing blood and other bodily fluids are aspirated to keep the surgical site clean and ensure adequate instrument visibility. While useful, aspiration is not only inefficient to implement, but it also requires several seconds to commence the aspiration process, which delay is unfortunately often decisive. As an alternative, use of forceps to insert absorbent plugs through a trocar at the surgical site has been found similarly inefficient.

In one arrangement, an instrument is provided for inserting a haemostatic plug into the abdominal cavity during laparoscopic surgery. Such instrument includes a tubular element for receiving a plug of haemostatic material and a sliding plunger for applying the plug directly where bleeding has occurred.

One disadvantage of these arrangements is that recovery of the plug using a forceps can be laborious and even dangerous, especially during laparoscopic surgery for removal of a tumor. More specifically, during this procedure, the dissemination of cells, including those that may be cancerous, as is caused by partial squeezing of the plug as it passes through the trocar, may take place at a site far from where the tumor developed. Such dissemination, in turn, may cause serious remote neoplastic dissemination which is difficult to treat. Because the plug becomes soaked with blood or other bodily fluids, there is also considerable risk that the surgeon may either be unable to find and remove the plug, or will simply "forget" about the plug after it has been introduced into a patient's body cavity, often leading to medical and legal disputes. While these disputes are generally less frequent in laparoscopic surgery than in traditional or "open" surgery, the risk is still considered significant.

OBJECTS AND SUMMARY OF THE INVENTION

Accordingly, it is an object of the present invention to provide a device for removing organic fluids from a patient's body cavity during a medical procedure that overcomes inefficiencies and delays attendant aspiration of such fluids, avoids the inefficient, laborious and hazardous nature of inserting absorbent plugs using forceps, and eliminates the risk of oversight associated with plug removal during the procedure.

It is another object of the present invention to provide a device for inserting an absorbing plug into a patient's abdominal cavity during laparoscopic surgery, which also allows the plug to be safely and easily located at the surgical site, thereby facilitating its recovery after use and avoiding the risk of its loss at the surgical site (and, hence, being left in the patient's body) as well as avoiding possible cell dissemination remotely to the site.

It is a further object of the present invention to provide a haemostatic plug that may be easily retrieved and recovered after use.

According to one aspect of the present invention, a device is provided for removing organic fluids from a patient's body cavity during endoscopic surgery. The device comprises an absorbing plug, a tubular body suitable for slidingly housing the plug, and a plunger slidingly engageable in the tubular body so as to push the plug outside thereof and place it at the surgical site. The tubular body and plunger have a distal end and a proximal end. The plug is preferably connected to a radio-opaque plug locator ball for floating relative to internal organs, blood or other fluids present at the surgical site. At the distal end of the plunger, a handle is provided for gripping the ball and recovering the plug after use by retracting the plunger inside the tubular body.

In accordance with another aspect of the present invention, a device is provided for removing organic fluids from a body cavity. The device comprises an absorbing plug, a tubular body suitable for slidingly housing the plug, and a plunger slidingly engageable in the tubular body so as to push the plug outside thereof and place it at the surgical site. The tubular body and plunger have a distal end and a proximal end, wherein the plug is connected to at least one radio-opaque plug locator ball for floating relative to internal organs, blood or other fluids present at the surgical site. A loop is provided at the distal end of the plunger, and at the proximal end, a first handle is provided for actuating the plunger so as to grip the ball and recover the plug after use by retracting the plunger inside the tubular body. At the proximal end of the tubular body and of the plunger, a second handle is associated with the tubular body for actuating axial sliding of the plunger in one direction or the other as a result of corresponding pressure actions exerted simultaneously in opposite directions on the second handle.

BRIEF DESCRIPTION OF THE DRAWINGS

A specific, illustrative device for endoscopic surgery, according to the present invention, is described below with reference to the following drawings, in which.

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
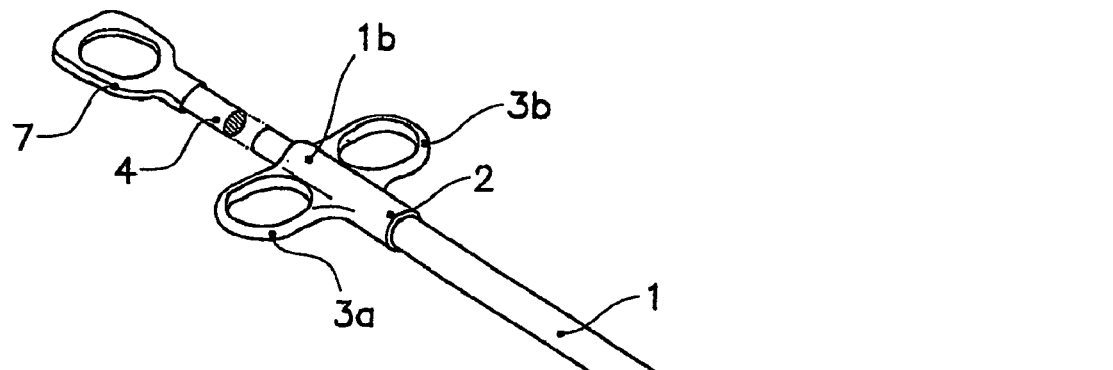
FIG. 1 is a partial perspective view of a surgical device, according to one aspect of the present invention.
Figure 2:
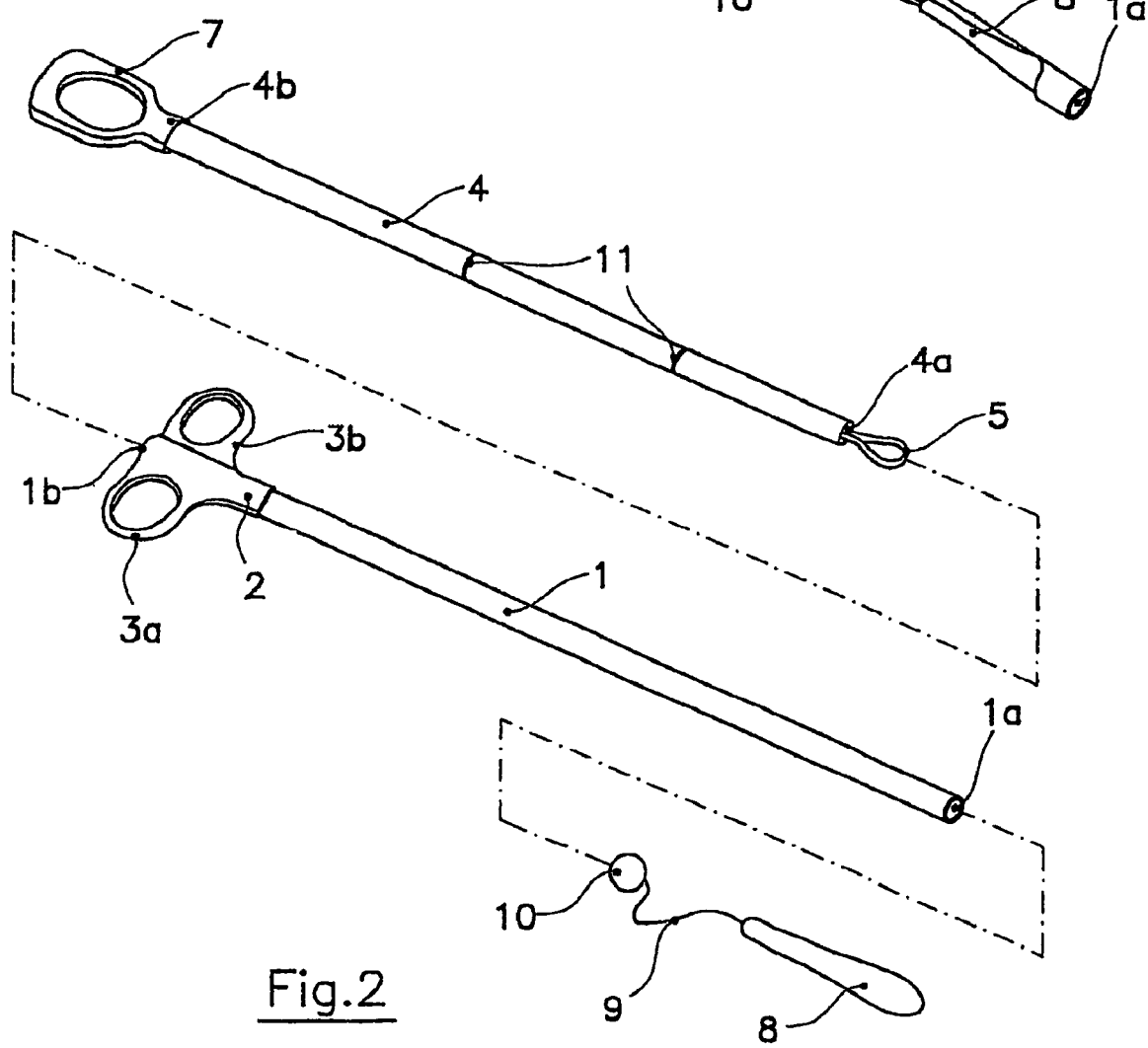
FIG. 2 is an exploded perspective view of the device shown in FIG. 1.

Referring now to the drawings and, more particularly, to FIGS. 1-4c, there is shown generally a specific, illustrative, surgical device, in accordance with various aspects of the present invention. According to one embodiment, shown generally in FIG. 1, the device comprises a relatively rigid tubular sheath or body with open distal and proximal ends 1a and 1b, respectively. A proximal portion of the sheath is engaged proportionately firmly with a hub 2 having a second handle such as a plurality of diametrically opposing handle rings or annular grips 3a, 3b generally coplanar to the sheath.

Figure 3:
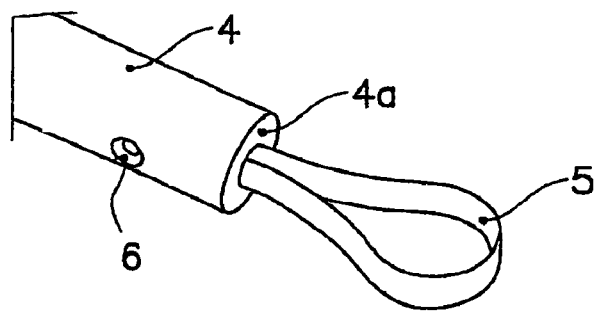
FIG. 3 is a detail view of the device illustrated in FIG. 1 showing the end portion of the plunger.

A stem or plunger 4 is slidingly inserted in tubular sheath 1, the distal end of which preferably has an eyelet configuration. According to one embodiment of the present invention, the distal end is constructed of a flexible thin plate 5 bent in half so as to form a loop with its ends connected to distal end 4a of the stem via a transverse peg 6 (as best seen in FIG. 3). Advantageously, plate 5 may be a strip of rectangular section and/or constructed of a selected harmonic or nickel-titanium steel to exhibit sufficient flexural rigidity. Proximal end 4b of stem 4 mounts an annular grip or first handle 7 which, in the present embodiment, is connected to the stem by a peg (not shown), e.g., made of steel, and co-planar therewith.

The tubular sheath and stem are preferably made of a selected metallic or polymeric material suitable for surgical use, for example, polyethylene, TEFLON and/or the like. Annular grips 3a, 3b and 7 are desirably constructed of a similar material. Circumferential grooves 11 are provided advantageously along stem 4 for housing O-rings (not shown) suitable for facilitating sliding along an internal lubricated surface of tubular sheath 1.

The device, according to the present invention, preferably also comprises an absorbent plug 8 having an elongated shape and, more particularly, a substantially pear-shape, such shape being suitable for enabling its insertion in the tubular sheath. Plug 8 is joined to a ball 10 by a wire 9, the ball (i) having a specific weight generally lower than that of blood such that it floats relative thereto, and (ii) being generally radio-opaque so as to be visible using X rays. The ball should preferably be colored so as to be visually identifiable within the surgical field and have a surface finish suitable for allowing blood to slide over its surface.

Generally speaking, the plug can be made of any material suitable for haemostasis, and for absorption of blood and any other liquid that may be present in the surgical field. Beneficially, the plug may be constructed of polyvinyl alcohol (PVA) as in a product available under the commercial names MERACEL, IVALON or other equivalent products. Additionally, wire 9 is made of a biocompatible material, such as suture thread, having a diameter of about 0.5 mm and a length generally within a range of 8 cm and 10 cm.

The dimensions of ball 10 are such as to allow its insertion into tubular sheath 1 and, in turn, determine the dimensions of the loop so formed at distal end 4a of stem 4, which dimensions must necessarily be slightly larger than those of body 10. The ball must also be radio-opaque and white in color (or yellow, or another light color) so as to be easily identified at the surgical site. Optionally, a plurality of additional balls are provided.

In operation, to locate the plug at the surgical site, tubular sheath 1 of the insertion device, where the plug had been placed previously, is introduced into the patient's abdominal cavity through a trocar. By sliding the stem, which operates like a plunger, the plug is pushed outside of the tubular sheath and located by the surgeon at the desired place of use. In this regard, it is considered desirable that the length of the stem be greater than or, at most, equal to that of the tubular sheath to ensure that eyelet end 4a of the stem projects fully from the sheath when the stem is fully inserted therein.

Figure 4A:
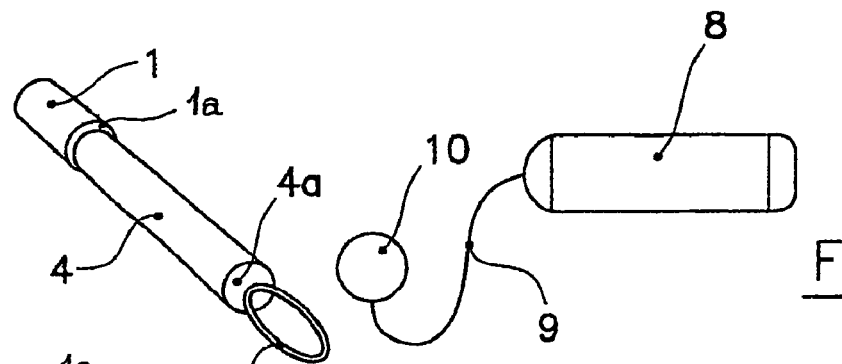
FIGS. 4a-4c illustrate steps of a method for recovery of a plug using the device shown in FIG. 1, according to one aspect of the present invention.
Figure 4B:
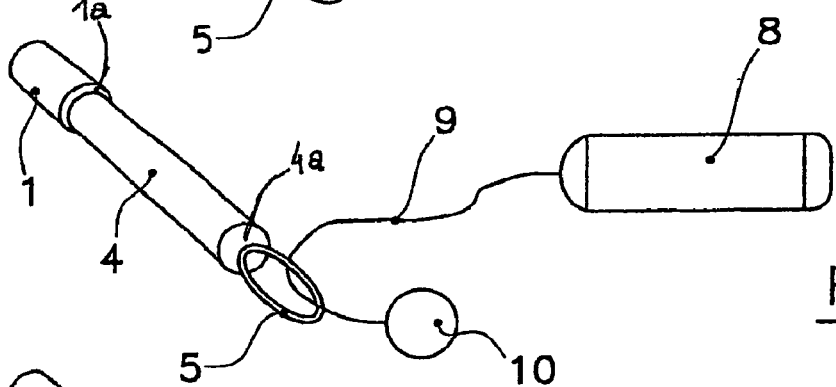
Figure 4C:
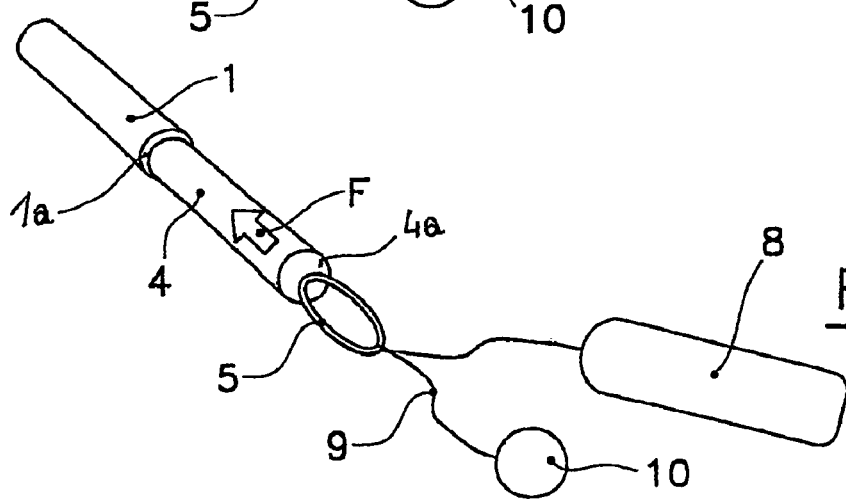

Once the plug has served its function, it must be recovered and removed from the abdominal cavity. To this end, as shown in FIGS. 4a, 4b and 4c, initially ball 10 is identified visually. Eyelet end 4a of the stem is then moved toward the ball such that it passes suitably through the loop and hooks wire 9 of the plug. Next, through light hand movements of the surgeon, the loop is caused to slide along the wire, pulling the stem backward, generally in the direction of arrow F in FIG. 4c, until the plug has returned to a position completely inside the tubular sheath. Thereafter, the device is disengaged from the trocar.

Overall, the present invention is particularly advantageous in that recovery of the plug and, more specifically, its reinsertion in tubular sheath 1 after use, is performed directly at the surgical site, so that partial squeezing of the plug, as inevitably occurs during use, does not become a source of remote contamination. Contamination is especially dangerous during removal of a tumor, namely, when tumoral cells are present, given the possibility of neoplastic dissemination and the risk of formation of metastasis. More specifically, partial squeezing of the plug, as a worst case scenario, is tantamount microscopically to incomplete removal of the tumor. Inevitably, with or without the plug, while this may still give rise to the possibly of a relapse of the disease locally, it is preferred when compared to the severity of remote metastasis.

Moreover, the loop hooking device of the present invention is considered highly desirable due to its simplicity and effectiveness. As those skilled in the art will appreciate, based on a review of this disclosure, other equivalent hooking devices may be utilized within the spirit and scope of the present invention.

Various modifications and alterations to the present invention may be appreciated based on a review of this disclosure. These changes and additions are intended to be within the scope and spirit of the invention as defined by the following claims.

What is claimed is:

1. A surgical device for removing organic fluids from a body cavity, the device comprising an absorbing plug, a tubular body suitable for slidingly housing the plug, and a plunger slidingly engageable in the tubular body so as to push the plug outside thereof and place it at the surgical site, the tubular body and plunger having a distal end and a proximal end, wherein the plug is connected to at least one radio-opaque plug locator ball for floating relative to internal organs, blood or other fluids present at the surgical site, a loop is provided at the distal end of the plunger, and at the proximal end of the plunger, a first handle is provided for actuating the plunger so as to grip the ball and recover the plug after use by retracting the plunger inside the tubular body.

2. The device set forth in claim 1, wherein the at least one ball is connected to the plug by a wire.

3. The device set forth in claim 2, wherein the at least one ball has relatively smaller dimensions than the inside of the tubular body.

4. The device set forth in claim 1, wherein the plunger includes a stem with the loop at a distal end thereof, the loop being generally wider than the locator.

5. The device set forth in claim 4, wherein the loop is formed by a relatively thin plate bent and connected at its ends to the distal end of the stem.

6. The device set forth in claim 1, wherein at the proximal end of the tubular body and of the stem, a second handle associated with the tubular body for actuating axial sliding of the stem in one direction or the other as a result of corresponding pressure actions exerted simultaneously in opposite directions on the second handle.

7. The device set forth in claim 6, wherein the second handle is of a ring type so as to allow its engagement with fingers of a user.

8. The device set forth in claim 7, wherein the second handle includes a pair of handle rings at the proximal end of the tubular body, the rings being generally diametrically opposite to and coplanar with one another, whereas at the proximal end of the stem, the first handle includes a handle ring, generally coplanar thereto.

9. The device set forth in claim 1, wherein the locator has a white or other relatively light colored surface.

* * * * *